United States Patent [19]

Denen et al.

[11] Patent Number: 5,400,267

[45] Date of Patent: Mar. 21, 1995

[54] LOCAL IN-DEVICE MEMORY FEATURE FOR ELECTRICALLY POWERED MEDICAL EQUIPMENT

[75] Inventors: Dennis J. Denen, Columbus; Philip E. Eggers, Dublin, both of Ohio; Robert F. Shaw, San Francisco, Calif.; Albert E. Weller, III, Columbus, Ohio

[73] Assignee: Hemostatix Corporation, Sausalito, Calif.

[21] Appl. No.: 986,967

[22] Filed: Dec. 8, 1992

[51] Int. Cl.6 .............................................. G06F 15/00
[52] U.S. Cl. ................................. 364/552; 364/413.01; 364/483; 128/908; 323/911; 307/31
[58] Field of Search .................. 364/413.07, 413.01, 364/480, 483, 550, 552; 365/226, 244; 439/909; 128/908; 323/911; 307/11, 31, 38, 39, 154

[56] References Cited

U.S. PATENT DOCUMENTS

| | | | |
|---|---|---|---|
| 4,621,643 | 11/1986 | New, Jr. et al. | 128/633 |
| 4,657,013 | 4/1987 | Hoerenz et al. | 128/303.1 |
| 4,700,708 | 10/1987 | New, Jr. et al. | 128/633 |
| 4,770,179 | 9/1988 | New, Jr. et al. | 128/633 |
| 4,822,997 | 4/1989 | Fuller et al. | 250/227 |
| 4,862,393 | 8/1989 | Reid et al. | 364/550 |
| 4,897,789 | 1/1990 | King et al. | 364/413.07 |
| 4,977,394 | 12/1990 | Manson et al. | 340/679 |
| 5,155,693 | 10/1992 | Altmayer et al. | 364/550 |
| 5,162,725 | 11/1992 | Hodson et al. | 324/115 |

*Primary Examiner*—Emanuel T. Voeltz
*Assistant Examiner*—Edward Pipala
*Attorney, Agent, or Firm*—Fish & Neave

[57] ABSTRACT

A non-volatile memory disposed within electrically powered medical equipment is described. The non-volatile memory may be preprogrammed to store utilization limits and parametric data for the equipment. An external control module may be programmed to store the utilization history for the equipment in the non-volatile memory on an on-going basis. The control module compares the utilization limits and utilization history during each use, and disables the equipment if a utilization limit is exceeded. The control module may also use the parametric data stored in the non-volatile memory to regulate the power supplied to the equipment.

46 Claims, 5 Drawing Sheets

SERIAL NUMBER

MODEL NUMBER

POWER SUPPLY PARAMETRIC DATA

VOLTAGE LIMITS
    CURRENT LIMITS
    INSTRUMENT IMPEDANCE
    VOLTAGE SET POINTS
    CURRENT SET POINTS
    VOLTAGE RANGES
    CURRENT RANGES
    SCALE FACTORS

LIMIT DATA

MAXIMUM PROCEDURE COUNT
    MAXIMUM ACTUATION COUNT
    MAXIMUM ACCUMULATED ACTUATION TIME
    MAXIMUM STERILIZATION COUNT
    MAXIMUM FAULT COUNT

UTILIZATION DATA

ACCUMULATED PROCEDURE COUNT AFTER
        THE MOST RECENT ACTUATION
    ACCUMULATED ACTUATION COUNT AFTER
        THE MOST RECENT ACTUATION
    ACCUMULATED ACTUATION TIME AFTER
        THE MOST RECENT ACTUATION
    ACCUMULATED STERILIZATION COUNT AFTER
        THE MOST RECENT STERILIZATION
    ACCUMULATED FAULT COUNT DURING THE
        CURRENT SURGICAL PROCEDURE

*FIG. 8*

LOCAL IN-DEVICE MEMORY FEATURE FOR ELECTRICALLY POWERED MEDICAL EQUIPMENT

This invention relates to improved electrically powered medical equipment, and particularly to electrically powered medical equipment comprising non-volatile memory.

BACKGROUND OF THE INVENTION

Many useful medical devices, both therapeutic and diagnostic, are electrically powered and include electrically powered control or sensing means. These devices frequently have only a limited useful life. The limited lifetime of these devices is determined as the period during which the devices can be relied upon to perform well, after which the devices must either be replaced or serviced. Examples of limited-use therapeutic devices are electrosurgical operating instruments such as electrocautery surgical diathermies and hemostatic scalpels, endoscopic devices such as laparoscopic scissors and probes, arthroscopic operating instruments and angioplasty reaming instruments. Examples of limited-use diagnostic devices are physiologic sensors, such as those used for the measurement or monitoring of physiological and biochemical parameters, (i.e. oxygen, glucose, etc.).

Conventional methods of tracking the remaining useful lifetime of therapeutic or diagnostic equipment consists principally of recording in a ledger the number of operations in which a device has been used, or the number of times the device has been sterilized, without regard to the actual usage of the device. Such recording systems are prone to bookkeeping errors, and may either overestimate or underestimate the condition of a device.

It would therefore be desirable to provide apparatus for more accurately tracking the usage of a limited-use medical device. The ability to track device usage would provide the capability for replacing a device before it fails, a vital consideration where the device is used in critical medical applications, such as surgical operations, or monitoring critically ill patients.

Similarly, it can be extremely important to track the usage of the more durable power supply/controller/measuring apparatus where important components may have need for periodic servicing and replacement of parts; again this need is especially important where vital medical procedures are being performed, such as surgical operations or monitoring of the critically ill. A simple workable system for accomplishing the usage of tracking and data accumulation for more durable power supply/controller/measuring apparatus is not currently available.

It would therefore be desirable to provide a system for more accurately tracking the usage of, and accumulating such usage data for, more durable power supply/controller/measuring apparatus that is used with limited-use medical devices.

In additions many durable electronic instruments used in conjunction with the limited-use devices noted above, such as electronic power supplies, controllers or measuring apparatus, may be used with more than one kind of the above-mentioned limited-use devices. Frequently, the electronic modes of operation differ, for example, constant voltage versus constant current, and the appropriate levels and limits for operating parameters of the electronic instruments differ depend upon the particular limited-use device being used. Thus, the surgeon or medical technician must be knowledgeable of the operating parameters for each type of limited-use device and set the mode of operation accordingly.

Conventional arrangements provide different connection ports on the power supply/controller/measuring apparatus for different limited-use devices (such as electrosurgical scissors versus electrosurgical scalpels). Alternatively, switching means are provided on the power supply/controller/measuring apparatus to accommodate the different demands of the various limited-use devices. However, the number of available connection ports of a power supply/controller/measuring apparatus is limited and switches may not be accurately set for a wide variety of reasons. Also, it may be possible to connect a limited-use device to an incompatible power supply/controller/measuring apparatus, thereby causing damage to both items.

It would therefore be desirable to provide a system that automatically verifies compatibility of a device with the power supply/controller/measuring apparatus when the device is connected thereto, and that automatically sets the power supply/controller/measuring apparatus to the appropriate operational parameters for the connected device, without having to dial in the particular operational parameters for that device.

In view of the foregoing considerations, it would be desirable to provide therapeutic and diagnostic medical systems having a non-volatile memory device for tracking and accumulating usage data. In addition, a non-volatile memory device associated with a limited-use medical device may be used to automatically set the operational parameters (or other parametric data) for the limited-use device when the device is connected to a power supply/controller/measuring apparatus. The non-volatile memory device in the limited-use would cooperate with control logic resident in the supply/controller/measuring apparatus to perform one or more of the following functions:

- identify the specific limited-use device and automatically establish its compatibility with the power supply/controller/measuring apparatus to which it is connected, prohibiting operation of those limited-use devices that are not compatible;
- establish the electrical mode in which the power supply/controller/measuring apparatus should be operated with the limited-use device, if more than one kind of limited-use electrical device can be used with the power supply/controller/measuring apparatus;
- establish the nominal electrical parameters for the particular mode selected at which the device should be operated and the limits of those electrical parameters beyond which the device should not be operated;
- maintain and continually update a history of critical operating parameters for the limited-use device, (e.g. cumulative number of times activated, cumulative amount of power dissipated, number of separate occasions on which device has been used, number of times device sterilized) that may be maintained as part of the limited-use device and that may be communicated to any power supply/controller/measuring apparatus with which the limited-use device can be used;
- maintain a schedule of limits for each of the foregoing critical operating parameters as part of each limited-use instrument which can be communicated to any power supply/controller/measuring apparatus with which the limited-use device can be operated;

maintain a program of actions to be undertaken by the power supply/controller/measuring apparatus when each of the limits has been reached (such as messages to be displayed or announced, or further operation to be prohibited); and maintain a record in each power supply/controller/measuring apparatus of the history of each and all of the limited-use devices that have been used with it.

SUMMARY OF THE INVENTION

In view of the foregoing, it is an object of the present invention to provide non-volatile memory disposed within medical equipment, that may be used to store data pertaining to the equipment. The in-device memory may be preprogrammed with identification data, which may be used to identify a particular instrument or component, or more generally, may be used to identify the equipment type. Such data may include, for example, the serial number or model number of the equipment.

The in-device memory of the present invention may also be preprogrammed with parametric data that may be used to define the power supply requirements of the medical equipment. Such data may include, for example, voltage limits, current limits, instrument impedance, voltage setpoints, current setpoints, voltage ranges, current ranges and scale factors which serve to limit the power supplied to a range acceptable for the equipment being used. Parametric data may also include a current or voltage limit indicative of a fault condition, and other data particular to the application of the device.

The in-device memory of the present invention may be further preprogrammed with manufacturer specified utilization limits, for example, a maximum procedure count or use count, a maximum equipment utilization count, a maximum equipment actuation time and a maximum sterilization count. The non-volatile, in-device memory of the present invention may also be used to store the utilization history of the medical equipment on an ongoing basis, including, for example, an accumulated procedure count or use count, an accumulated instrument actuation count, an accumulated actuation time and an accumulated sterilization count.

It is another object of the present invention to provide means for using the identification data stored in the in-device memory of the present invention to prevent incompatible components of multi-component electrically powered medical equipment from being used in combination, and to prevent electrically powered medical equipment from being used with incompatible power supplies. The in-device memory of the present invention may be connected to an external power supply and control apparatus that comprises a power supply and a control module. The control module may read the stored identifying information, including the serial number and model number, of each component connected to the power supply and control apparatus. It is contemplated that the control module will be programmed to disable the equipment if incompatibility among components, or with the power supply, is detected.

It is still another object of the present invention to provide means for using the parametric data stored in the in-device memory of the present invention to determine the power supply requirements of the medical equipment. The in-device memory of the present invention may be connected to an external control module, which may read the aforementioned parametric data, including, for example, voltage limits, current limits, instrument impedance, voltage setpoints, current setpoints, voltage ranges, current ranges and scale factors from the in-device memory. These parameters may be used by the power supply and control apparatus to regulate the power supplied in accordance with the needs of the medical equipment.

It is yet another object of the present invention to provide means for disabling medical equipment if a fault limit has been exceeded. It is contemplated that the control module will compare the manufacturer specified current or voltage limit stored in the in-device memory to the supplied current or voltage to determine if a fault has occurred. If a fault is detected, the control module may disable the equipment. If the number of faults that occurs during use exceeds a manufacturer specified limit, then the control module may prevent the power supply from being reset to attempt further use.

It is yet another object of the present invention to provide non-volatile memory disposed within medical equipment that may used to store information related to the utilization history of the equipment. The in-device memory of the present invention may be programmed immediately before, during and immediately after use, for example, during a surgical procedure, by a control module disposed within an external power supply and control apparatus. Thus, the in-device memory may store accumulated procedure count or use data, an accumulated equipment actuation count, an accumulated equipment actuation time, an accumulated sterilization count and other relevant data throughout the life-span of the equipment. The in-device memory of the present invention may be reprogrammed after a maintenance service has been performed; thus, the in-device memory may accumulate totals for the aforementioned parameters, among others, during each maintenance interval.

It is yet another object of the present invention to provide means for using the equipment utilization history stored in the in-device memory of the present invention to disable the equipment when a manufacturer specified utilization limit has been exceeded. The in-device memory of the present invention may be connected to an external control module, which may compare one or any combination of the aforementioned utilization limits to the corresponding accumulated values. Upon determining that a utilization limit has been reached, it is contemplated that the control module will disable the equipment, typically by preventing the power supply from delivering power to the equipment. As equipment utilization approaches a limit value, the control module provides the surgeon or medical technician with a "change equipment" advisory, so that the equipment can be replaced before it is disabled, thereby minimizing any impact of in-use replacement.

These and other objects are accomplished in accordance with the principles of the present invention by providing non-volatile memory disposed within medical equipment that may be used to store data pertaining to the equipment. The non-volatile memory may be disposed within a handle, an electrical connector or cable, or any other portion of the equipment having dimensions suitable for housing the non-volatile memory and its related circuitry.

The non-volatile, in-device memory of the present invention may be provided by any known non-volatile memory device having dimensions suitable for disposition in medical equipment. Such memory devices may include, for example, read only memory (ROM), programmable read only memory (PROM), erasable programmable read only memory (EPROM), flash memory, battery-backed-up random access memory (RAM), non-volatile RAM, magnetic data storage apparatus, including tape drives and disk drives, optical data storage apparatus and most preferably, electrically erasable programmable read only memory (EEPROM). For the purposes of this application, EEPROM is defined as any non-volatile, semiconductor memory device in which the memory cells may be written to and erased on a byte-by-byte basis. Flash memory is defined as any non-volatile, semiconductor memory device that is erasable only in block.

The non-volatile memory device selected depends upon which of the above-described objects are desired for a particular application, and the size of the medical equipment. Non-volatile memory devices that are not programmable during use, for example, ROM, PROM, EPROM and flash memory, may be suitable where it is desired that the equipment provide the control module with a predetermined power profile, i.e., parametric data, or product compatibility data, i.e., identification data. In this instance, it is sufficient that the memory provide data that can be read by the control module, but that need not be updated. On the other hand, non-volatile memory devices that offer read and write capability while power is supplied, and data retention when the equipment is not being supplied with power, for example, EEPROM, non-volatile RAM, battery-backed-up RAM, magnetic data storage apparatus and optical data storage apparatus, are necessary when it is desired to write data to the memory reflecting current usage. Both types of memory devices are suitable for use in medical equipment constructed in accordance with the present invention, since the equipment are typically disconnected from an external power supply after each use.

Larger non-volatile memory devices, for example disk drives, tape drives, optical data storage devices and battery-backed-up RAM may be suitable for medical equipment having sufficient space to house such components. For example, an external power supply and control apparatus may be considered a component by itself, also having utilization limits and maintenance schedules that must be adhered to. Any of the aforementioned larger non-volatile memory devices would be suitable for such equipment. Conversely, smaller non-volatile memory devices are suitable where the memory must be disposed within smaller housings, for example, handles or electrical connectors.

It is desirable for the memory device selected for use in medical equipment to be independently addressable when several devices are connected to the same communication bus. As discussed heretofore, electrically powered medical equipment may share detachable components, particularly electrical connecting cables. Each component may have data storage requirements that differ from others concurrently being used. Furthermore, each component must be independently addressable in order to read identification data from each, to determine compatibility among the components and the power supply.

It is contemplated that the non-volatile, in-device memory of the present invention will be connected to an external power supply and control apparatus by communication bus comprising communication wires. The communication wires are typically located within the electrical connecting cable that is used to connect an external power supply and control apparatus to the equipment. The external power supply and control apparatus comprises a control module that controls the flow of data from, or to and from, the in-device memory, and may perform additional functions. The control module may comprise a microprocessor and random access memory (RAM), and may have access to programmable and non-programmable non-volatile memory in the external power supply and control apparatus.

Immediately after the equipment is energized by the external power supply and control apparatus, the control module interrogates the in-device memory for the aforementioned identification data, parametric data, and possibly the utilization limits and corresponding utilization history. The identification data is used immediately by the control module to determine compatibility among components, and with the power supply. The parametric data is used by the control module to set power supply ranges appropriate for the connected equipment and to determine current or voltage limits for fault detection. The control module may be programmed to compare the accumulated utilization history to the corresponding utilization limits. If a limit has been exceeded, the control module disables the equipment by preventing the power supply from energizing the equipment.

The control module may be required to disable the equipment before use begins, if a utilization limit had been reached during a previous use. In addition, the control module may disable the equipment during use. In either event, the control module provides the surgeon or medical technician with a "change instrument" advisory. The control module will first issue the advisory before the instrument reaches a utilization limit, so that the equipment can be conveniently replaced. The advisory may include an audible alarm, a visible warning light, a message display, or any combination thereof.

In an alternative embodiment, the control module performs write operations on the non-volatile in-device memory while the electrically powered medical equipment is connected to an external power supply and control apparatus. For example, once the equipment is connected to the power supply and energized, the control module writes to areas of memory containing data related to sterilization count. During use, for example, in a surgical procedure, the control module updates the accumulated utilization history. Alternatively, the control module may store utilization data associated with the current use in volatile memory, and update the accumulated utilization history in the in-device memory at the end of the use is terminated.

Thus, the control module reads data from the in-device memory, and controls operation of the connected medical equipment in accordance with the data that is read. The control module may also write data to the in-device memory that determines future use of the equipment, for example, if the maximum sterilization count is reached.

BRIEF DESCRIPTION OF THE DRAWINGS

The above and other objects and advantages of the invention will be apparent upon consideration of the following detailed description, taken in like reference numerals refer to like parts throughout, conjunction with the accompanying drawings, in which and in which.

DETAILED DESCRIPTION OF THE INVENTION

Figure 1:
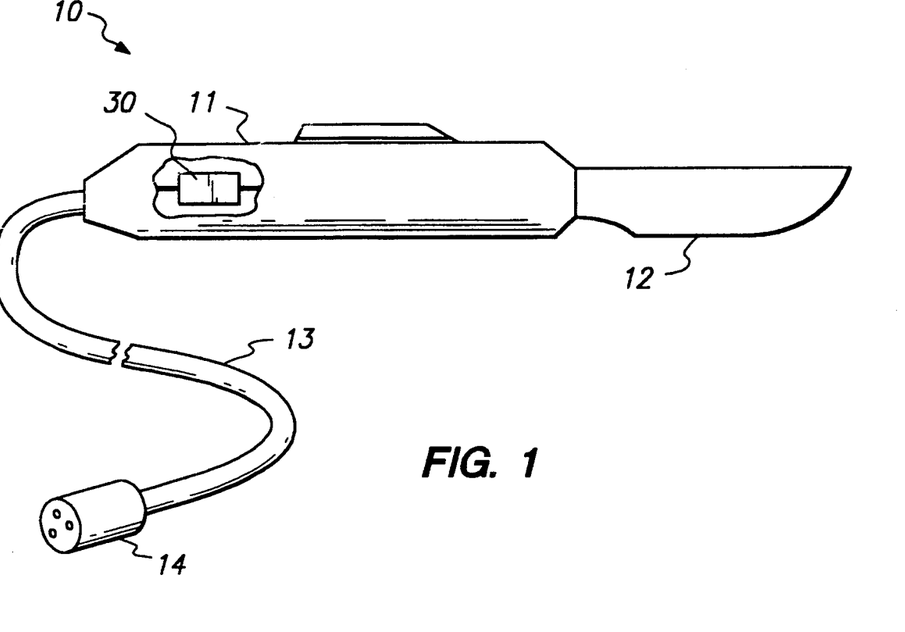
FIG. 1 shows, partly in section, an electrically powered medical instrument incorporating the in-device memory of the present invention.

Referring to FIG. 1, an illustrative embodiment of an electrically powered medical device having a non-volatile memory is described. Device 10 comprises an electrically-powered scalpel having handle 11, blade 12, cable 13, and connector 14. Device 10 is merely one illustration of an electrically powered medical device, and those skilled in the art will immediately recognize applicability of the present invention to a vast array of electrically powered medical devices. Electrical cable 13 terminates at connector 14, which connects device 10 to an external power supply and control apparatus, described hereinafter. In accordance with the present invention, non-volatile memory 30 may be disposed within handle 11, or connector 14, of device 10. Of course, the present invention may also be practiced with an instrument having reusable handle 11, so that the memory device is disposed within the reusable handle. In addition, as will be described hereinafter, certain objects of the present invention may be accomplished if a non-volatile memory device is disposed within blade 12, even if blade 12 is disposable.

Figure 2:
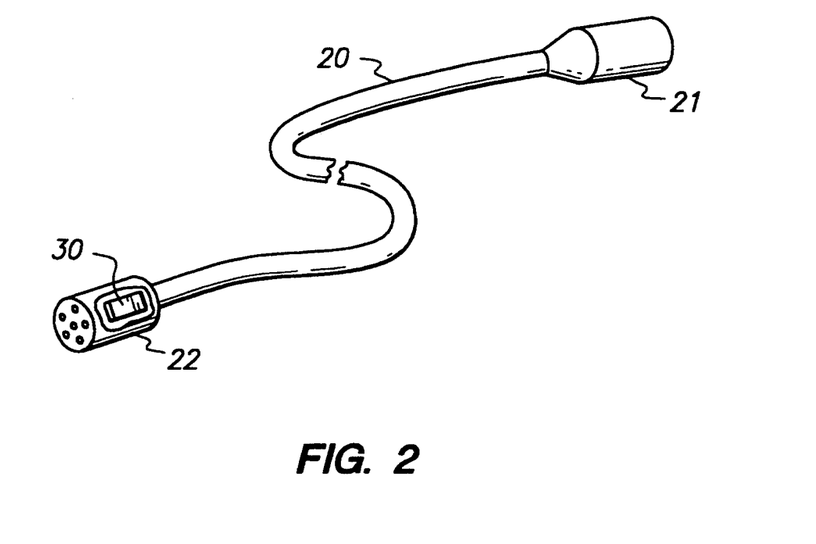
FIG. 2 shows, partly in section, a detachable electrical connecting cable in which the in-device memory of the present invention may be disposed within an electrical connector.

FIG. 2 depicts a reusable connecting cable 20, which may be used interchangeably with a number of compatible medical instruments. Reusable Connecting cable 20 terminates at each end with electrical connectors 21 and 22. Non-volatile memory 30 of the present invention may be disposed within either electrical connector 21 or 22 (as shown in FIG. 2) to store data pertaining to use of the cable.

Figure 3:
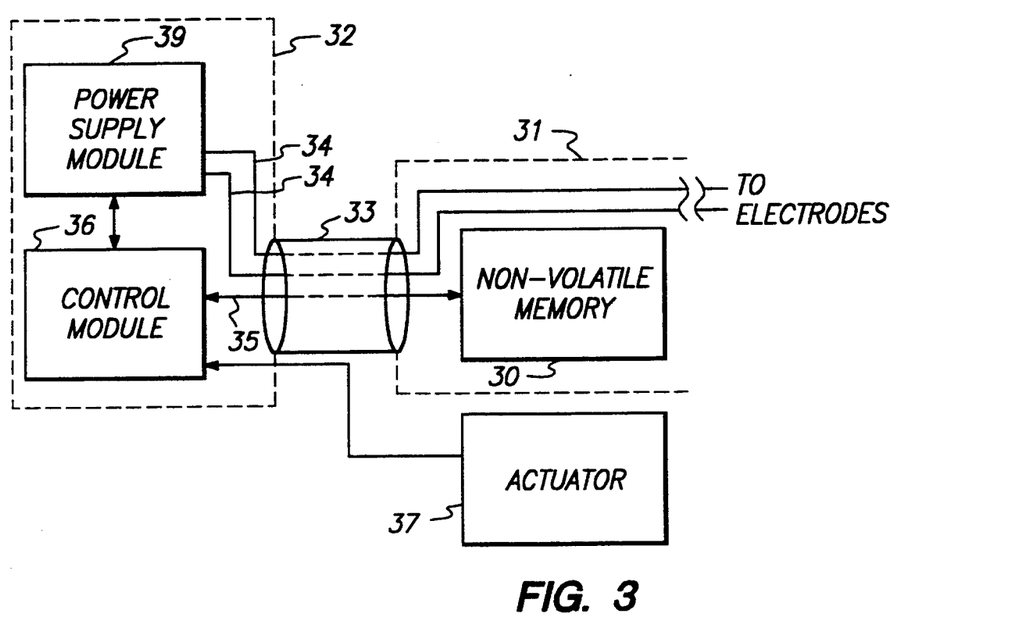
FIG. 3 is a block diagram showing an illustrative embodiment of a data storage and control apparatus for electrically powered surgical equipment comprising the in-device memory of the present invention.

Referring now to FIG. 3, non-volatile memory 30, which may be disposed within medical equipment 31, is connected to external power supply and control apparatus 32 by connecting cable 33. For example, for a bipolar electrosurgical instrument, at least two conducting wires 34 disposed within cable 33 are used to supply current to the instrument to perform cutting and coagulating functions; however, the number of conducting wires may vary depending upon the type of medical equipment.

Control module 36 communicates with non-volatile memory 30 via communication bus 35, also disposed within cable 33. In a preferred embodiment, control module 36 comprises a microprocessor, for example, the 68HC11 microprocessor, commercially available from Motorola, Inc. of Schaumburg, Ill. Alternatively, control module 36 may comprise a primary microprocessor and a secondary microprocessor. The primary microprocessor may be the Motorola 68HC11 and the secondary microprocessor may be, for example, the 16C54 microprocessor available from Microchip Technology, Inc. of Chandler, Ariz. The use of a secondary microprocessor is advantageous where non-volatile memory 30 comprises a non-volatile memory device that may be programmed during use, because the erase/write cycle of such a device, for example an EEPROM, may be as long as 5 msec. This delay may be excessive for practical applications, particularly since the primary microprocessor may be responsible for several other control functions associated with the operation of equipment 31. When a secondary microprocessor is used, the primary microprocessor issues a read or write request to the secondary microprocessor. The secondary microprocessor then completes the data transfer with non-volatile memory 30, so that the primary microprocessor may perform other tasks while the data transfer between the secondary microprocessor and non-volatile memory 30 is performed.

Figure 8:
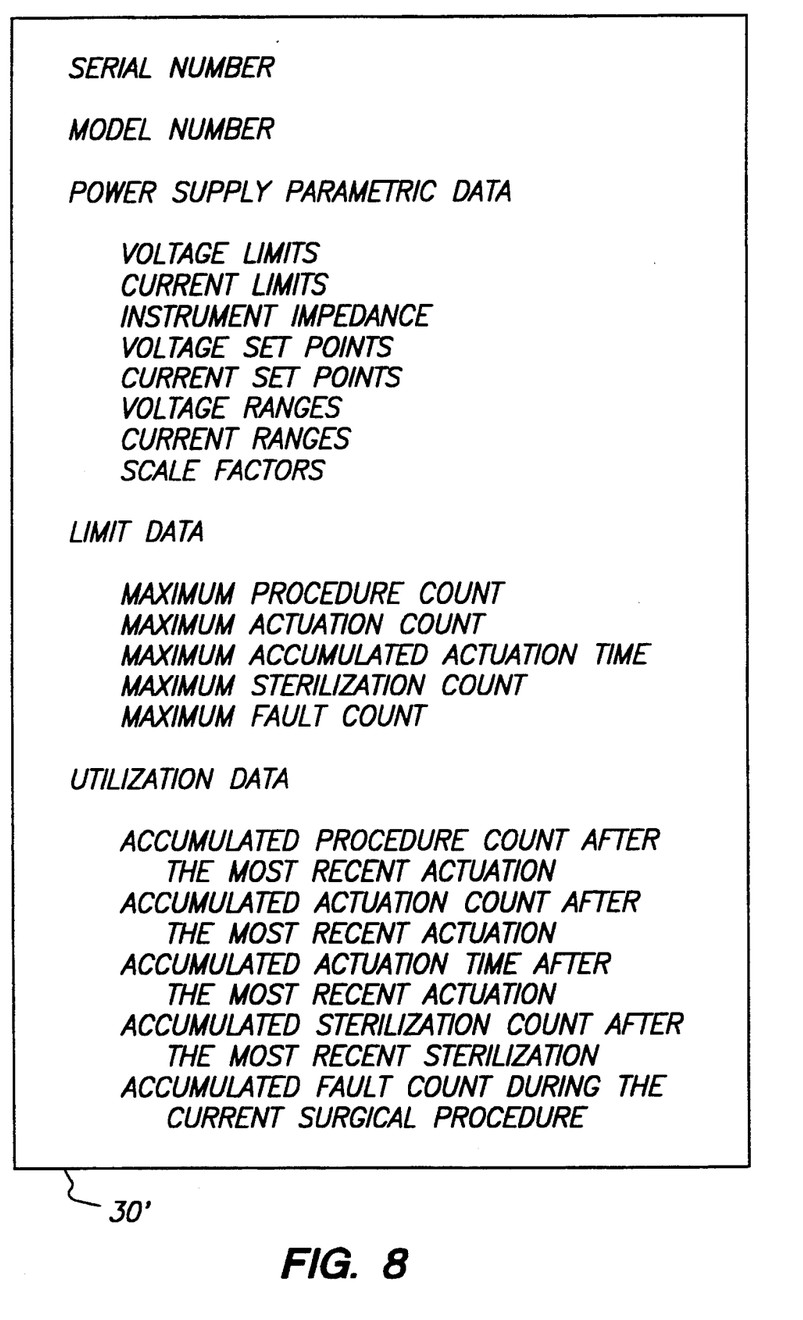
FIG. 8 is a block diagram indicating the various types of information that may be stored in non-volatile memory 30 of FIG. 3 and non-volatile memories 40 and 48 of FIG. 4.

Non-volatile memory 30 may comprise any device known to provide non-volatile memory to store various data 30' as shown in FIG. 8, described in detail hereinbelow. Preferably, non-volatile memory 30 is selected from a group of non-volatile memory devices that may be programmed during use, including but not limited to EEPROM, non-volatile RAM, battery-backed-up RAM, magnetic data storage apparatus and optical data storage apparatus. Alternatively, as will be shown hereinafter, certain objects of the present invention may be accomplished if non-volatile memory 30 is selected from a group of non-volatile memory devices that are not programmable during use. Such devices include, but are not limited to ROM, PROM, EPROM and flash memory.

Referring still to FIG. 3, it is contemplated that non-volatile memory 30 will be programmed with identification data that can be used by control module 36 to identify equipment 31. Such identification data may include a serial number, which uniquely identifies equipment 31, a model number, which identifies the equipment type, and other proprietary data programmed by the manufacturer. The preprogrammed identification data stored in non-volatile memory 30 may be used to ensure compatibility between equipment 31 and external power supply and control apparatus 32. After equipment 31 is connected to external power supply and control apparatus 32, control module 36 interrogates non-volatile memory 30 for identification data. Control module 36 may be programmed to compare the received identification data to corresponding data stored in control module 36. If the identification data stored in non-volatile memory 30 does not successfully compare to the corresponding data stored in control module 36, then control module 36 may disable power supply module 39, thereby rendering connected equipment 31 inoperable.

Medical equipment 31 may comprise a plurality of electrically powered components, each having non-volatile memory 30 disposed within. Control module 36 may be programmed to perform a compatibility check on all components of equipment 31, by comparing the identification data stored within each non-volatile memory 30. Each of the aforementioned compatibility checks, either with respect to power supply and control apparatus 32, or among components of equipment 31, may be performed when non-volatile memory 30 comprises any of the aforementioned non-volatile memory devices, whether or not they may be programmed during use.

Non-volatile memory 30 may also be preprogrammed with parametric data that may be used by control module 36 to control the operation of power supply module 39, to conform with the power supply requirements of equipment 31. Control module 36 may comprise a microprocessor to control the operating characteristics of power supply module 39, so that once equipment 31 is connected to power supply and control apparatus 32, control module 36 may request a transfer of preprogrammed parametric data stored in non-volatile memory 30. This data is then used by control module 36 to regulate the power supplied by power supply module 39 in accordance with the transferred parametric data. The parametric data may include, for example, voltage limits, current limits, instrument impedance, voltage setpoints, current setpoints, voltage ranges, current ranges and scale factors. Power supply regulation may be accomplished when non-volatile memory 30 comprises any of the aforementioned non-volatile memory devices, whether or not they may be programmed during use.

Power supply module 39 may be designed to serve a wide variety of medical equipment having different power requirements. Control module 36 is programmed to limit the power supplied by power supply module 39 to a level or range acceptable for that equipment, as defined by the parametric data read from the non-volatile memory. For example, some types of surgical equipment permit the surgeon to vary the power supplied to the equipment, usually by manipulating control knobs or switches on the front panel of power supply and control apparatus 32. However, when several different instruments share power supply and control apparatus 32, power supply module 39 may be required to provide different current or voltage ranges. Control module 36 may be programmed to use a scale factor read from non-volatile memory 30 in an appropriate algorithm to limit the power available from power supply module 39 to a range acceptable for equipment 31, while providing the surgeon with the full range of manual control.

Referring still to FIG. 3, preprogrammed parametric data stored in non-volatile memory 30 may be used by appropriately programmed control module 36 to establish electrical fault limits for equipment 31. Parametric data transferred from non-volatile memory 30 to control module 36 may include current or voltage limits. These limits, if exceeded, indicate a fault condition, such as a high current or voltage duration greater than a predefined value. The parametric data may also include a fault count limit, which if exceeded, results in equipment deactivation. Control module 36 may be programmed to monitor the current or voltage being supplied by power supply module 39. If the current or voltage being supplied to equipment 31 exceeds the corresponding limit, control module 36 begins to clock the duration of the high current or voltage condition. If the duration exceeds the corresponding high current or voltage duration, a fault is registered, and control module 36 disables power supply module 39. Typically, power supply module 39 may be reset by the physician or medical technician, thereby allowing continued use of the equipment. However, if the number of faults during use exceeds the aforementioned fault count limit, control module 36 may disable power supply module 39, and prevent it from being reset. In addition, control module 36 may be programmed to write a fault status flag to non-volatile memory 30, to prevent any future attempts at using equipment 31 until it has been serviced. It is contemplated that the fault status flag will be interrogated by control module 36 immediately after equipment 31 is energized, and if set, will result in control module 36 disabling power supply module 39.

Fault detection and equipment deactivation may be accomplished when non-volatile memory 30 comprises any of the aforementioned non-volatile memory devices, whether or not they may be programmed during use. However, if it is desired to set the aforementioned status flag to prevent future use of equipment 31, non-volatile memory 30 should comprise a non-volatile memory device that is programmable during use, for example, non-volatile RAM, battery-backed-up RAM, magnetic data storage apparatus, optical data storage apparatus or most preferably, EEPROM. Alternatively, as described hereinafter, non-volatile memory 30 may comprise a non-volatile memory that is not programmable during use, if second non-volatile memory that is programmable during use is provided elsewhere in the equipment, preferably, in power supply and control apparatus 32.

Referring still to FIG. 3, a method for limiting the use of electrically powered medical equipment to manufacturer specifications is described. In addition to identification data and parametric data, it is contemplated that non-volatile memory 30 will be preprogrammed with equipment utilization limits before equipment 31 is distributed by the manufacturer. The utilization limits include a maximum procedure count, a maximum equipment actuation count, a maximum equipment actuation time and a maximum sterilization count.

In a preferred embodiment of the present invention, non-volatile memory 30 is programmable during use, and comprises memory space dedicated to storing data reflecting the utilization of the equipment. The utilization history includes accumulated procedure count or use data, an accumulated equipment actuation count, an accumulated equipment actuation time, an accumulated sterilization count and any other data deemed relevant by the manufacturer. Control module 36 may be programmed to update the utilization history immediately before, during or immediately after use, as long as equipment 31 is energized.

When equipment 31 is energized, control module 36 reads the aforementioned utilization limits and the accumulated utilization history stored in non-volatile memory 30. In order to facilitate recording of equipment utilization during use, for example in a surgical procedure, it is preferable for control module 36 to store the accumulated utilization history in volatile memory available in control module 36, because the erase/write cycle of non-volatile memory 30 may be significantly longer than the write cycle of conventional RAM disposed within control module 36. Furthermore, the proximity of high frequency signals in connecting cable 33 on conducting lines 34 may interfere with communication signals sent by control module 36 on communication bus 35. The accumulated utilization history stored in non-volatile memory 30 may be updated at predetermined intervals throughout the procedure, or at the end of the procedure, but before the supply of power to equipment 31 is interrupted.

Control module 36 may use the accumulated utilization history and the utilization limits to disable equipment 31 once the manufacturer recommended utilization limits have been exceeded. Control module 36 compares each utilization limit to its corresponding value in the accumulated utilization history. For example, equipment 31 may be a surgical instrument having an actuation count limit of 150 actuations. Control module 36 will compare the actuation count limit of 150 to the total actuation count that has been previously accumulated from earlier surgical procedures and stored in non-volatile memory 30. If the total actuation count equals or exceeds 150, control module 36 sends a disabling message to power supply module 39. Power supply module 39, the circuitry of which may otherwise be a conventional power source for use with electrically powered surgical equipment, will not supply power to equipment 31 upon receipt of a disabling message from control module 36.

Similar programming may be used to determine if the accumulated actuation time exceeds the corresponding utilization limit. It may also be desirable to program control module 36 to perform more complicated comparisons between the utilization limits and their corresponding values in the accumulated utilization history. Since the accumulated equipment actuation count and the accumulated actuation time may combine to contribute to equipment deterioration more rapidly than either parameter individually, an algorithm utilizing both values may be programmed into control module 36 and used to disable equipment 31.

Additional utilization limits may be programmed and used to disable equipment 31. For example, chronological time, independent of actual equipment utilization, may contribute to equipment deterioration. It would be a straightforward application of the principles of the present invention to program non-volatile memory 30 with a date of manufacture, or maintenance service dates, and to provide control module 36 with an internal clock/calendar. The manufacture and maintenance service dates may be read by control module 36 as previously described, and compared to the clock/calendar. In accordance with the principles of the present invention, a manufacturer may program and use additional utilization limits that are appropriate for particular medical equipment.

If control module 36 determines that utilization limits have not been exceeded, power supply module 39 is permitted to supply power to the connected equipment. Control module 36 may be programmed to then monitor equipment utilization during use, so that control module 36 receives input from actuator 37 during the use. Such input may be supplied by a foot pedal, or a switch on the handle of equipment 31. Hence, control module 36 may be programmed to track the number of equipment actuations and the total equipment actuation time during use, for example in a surgical procedure. Control module 36 is programmed to accumulate equipment utilization data from the current use. At the end of the use, but before the supply of power to equipment 31 is interrupted, or at predetermined intervals, control module 36 updates the utilization history in non-volatile memory 30.

In another preferred embodiment, control module 36 is programmed to update the utilization history in non-volatile memory 30 after each actuation has been completed. For example, control module 36 may be programmed to increment the accumulated actuation count and increase the accumulated actuation time stored in non-volatile memory 30. The accumulated actuation count is incremented by one count after each actuation, and the accumulated actuation time is increased by the duration of the preceding actuation. Using this method, non-volatile memory 30 maintains an accurate utilization history throughout the duration of the current application. Thus, in the event of a power failure, or unexpected disconnection of equipment 31, the utilization of equipment 31 during the preceding use is properly recorded.

The principles of the present invention may also be used to disable equipment 31, after it has been subjected to a number of sterilization procedures that exceed a preprogrammed limit. One implementation of a sterilization counter scheme might assume, first, that the equipment is sterilized after each use and second, that external power supply and control apparatus 32 is not turned off during a single use.

After equipment 31 is connected to external power supply and control apparatus 32 by connecting cable 33, control module 36 reads from non-volatile memory 30 identification data and the aforementioned utilization limits, which may include a sterilization limit, and the accumulated sterilization count. The identification data may include a serial number that uniquely identifies equipment 31. Control module 36 may be programmed to write the serial number to volatile memory disposed within control module 36, if that serial number has not already been read during the current use. If the serial number has not been read during the current use, this condition indicates that equipment 31 is being used for the first time since the previous application, and in accordance with the first assumption above, it must have been sterilized since the previous use. Control module 36 may be programmed to then increment the accumulated sterilization count in non-volatile memory 30, and to compare the new sterilization count to a preprogrammed sterilization limit in non-volatile memory 30, which may have been transferred to volatile memory disposed within control module 36, along with other utilization limits. If the accumulated sterilization count meets or exceeds the sterilization limit, control module 36 disables power supply module 39 so that equipment 31 cannot be used until serviced.

An alternative implementation of a sterilization counter scheme might instead assume that the equipment is sterilized after each use, and that sterilization will have been performed after a pre-set period, for example, 5 hours. This pre-set period may depend on the type of medical equipment and its typical expected use period.

In this alternative scheme, the first time equipment 31 is connected to external power supply and control apparatus 32 during a current use, the time and date are written to non-volatile memory 30. Each time thereafter that the instrument is reconnected or energized, the control module reads the time and date stored in non-volatile memory. If less than the preset period has elapsed since the last connection or actuation of the device, the control module retains the sterilization counter at its current value. If the date and time indicate an elapsed time greater than the pre-set period, the control module increments the sterilization counter by one. If in this case the sterilization counter value is less than the preprogrammed sterilization limit, the control module updates the date and time stored in non-volatile memory 30 to the current date and time. When the sterilization counter equals the preprogrammed sterilization limit, the equipment is disabled and a "change instrument" advisory is displayed by the control module.

The above-described methods for disabling equipment 31 when utilization limits have been exceeded use two values for each limit—a preprogrammed utilization limit, and an accumulated utilization count. However, in order to conserve memory in non-volatile memory 30, it is preferable to store only one value for each utilization limit and decrement each preprogrammed utilization limit as the equipment is used. For example, the first time equipment 31 is used, the original, preprogrammed utilization limits will be stored in non-volatile memory 30. Control module 36 is programmed to decrement each preprogrammed limit during each use. Thus, non-volatile memory 30 maintains information related to available use remaining for equipment 31, instead of utilization limits and accumulated utilization counts.

In accordance with this method, control module 36 may be programmed to read the available use values immediately after equipment 31 is connected to external power supply and control apparatus 32. If an available use value has reached zero, control module 36 disables power supply module 39, thereby preventing further use of equipment 31. Alternatively, control module 36 may be programmed to perform a more complicated computation using some or all of the available use values to determine if equipment 31 should be disabled.

Control module 36 may be programmed to issue a change instrument advisory when equipment utilization approaches or reaches a utilization limit. As heretofore described, when equipment 31 is initially energized, control module 36 will determine if a limit has been reached. In addition to disabling equipment 31 if a limit has been reached, control module 36 may issue a change equipment advisory, thereby prompting the physician or medical technician to replace the equipment before putting the equipment into service. Furthermore, control module 36 may be programmed to issue the change equipment advisory before a utilization limit is reached, for example, by comparing the utilization history to values representing predetermined percentages of the utilization limits. Alternatively, non-volatile memory 30 may comprise a second set of utilization limits that are used by control module 36 to determine when a change equipment advisory should be issued.

The change equipment advisory may include an audible alarm, a visible warning light, a message display, or any combination thereof. Preferably, the advisory means are located in power supply module 39, or in equipment 31. Thus, control module 36 determines when an advisory should be issued, and sends a message to power supply module 39 or equipment 31, which in turn activates the advisory means.

Figure 4:
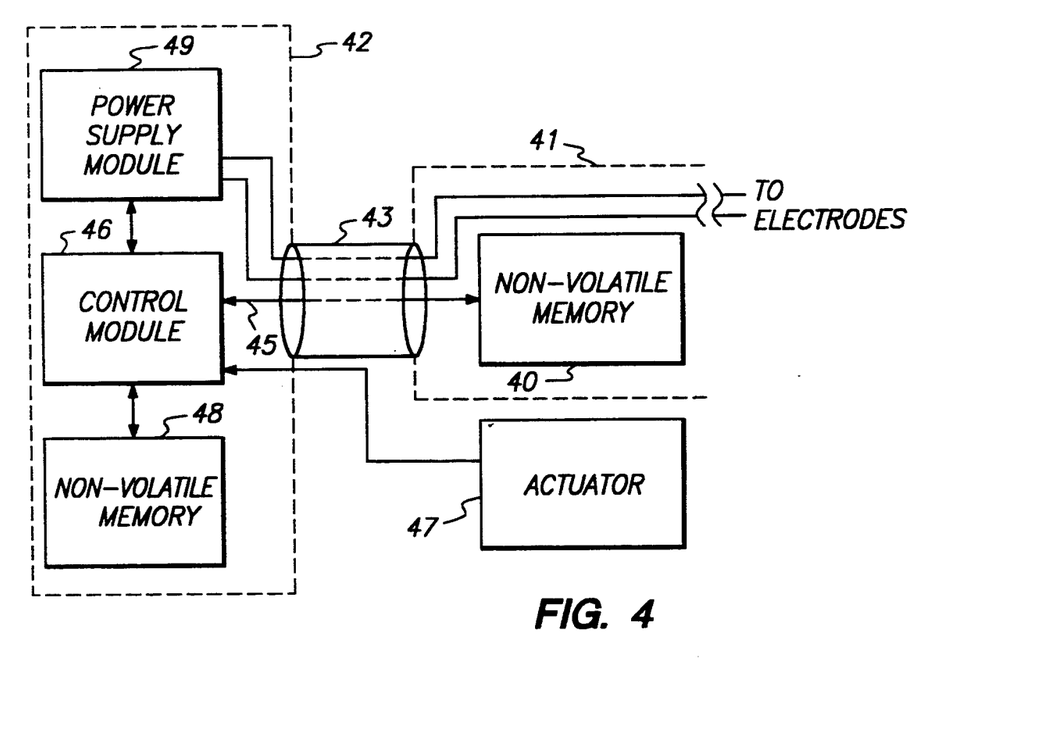
FIG. 4 is a block diagram showing an alternative embodiment of a data storage and control apparatus for electrically powered medical equipment.

Referring now to FIG. 4, an alternative embodiment of the present invention is described in which non-volatile memory 40 is selected from a group of non-volatile memory devices that are not programmable during use, including ROM, PROM, EPROM and flash memory, and power supply and control apparatus 42 comprises non-volatile memory 48 that is programmable during use. Non-volatile memory 48 performs one of the same functions in this embodiment as non-volatile memory 30 of the previously described embodiment, namely, to store data tracking usage of equipment 41. Thus, non-volatile memory 48 may comprise EEPROM, non-volatile RAM, battery-backed-up RAM, magnetic data storage apparatus or optical data storage apparatus.

Non-volatile memory 40 is preprogrammed by the manufacturer with identification data and parametric data, as hereinbefore described. The identification data may be used by control module 46 to determine if equipment 41 has been used in previous applications. Non-volatile memory 48 is configured so that memory space is allocated for each equipment component that is used in conjunction with power supply and control apparatus 42. The first time equipment 41 is energized by power supply and control apparatus 42, control module 46 reads non-volatile memory 48 to determine if the identification data stored in non-volatile memory 40 has been previously written to non-volatile memory 48. If the identification data is not found, control module 46 allocates memory space in non-volatile memory 48 to equipment 41, and writes the identification data associated with equipment 41 to that memory space.

As equipment 41 is used, its utilization history is stored in the memory space allocated in non-volatile memory 48, using the principles described heretofore with respect to FIG, 3. As equipment 41 is used, control module 46 monitors actuator 47, and compares the accumulated utilization history, which includes an accumulated procedure count, an accumulated actuation count, an accumulated actuation time and an accumulated sterilization count, to the utilization limits stored in non-volatile memory 40. Control module 46 is programmed to send a disabling message to power supply module 49 when a utilization limit has been exceeded. Alternatively, the utilization limits stored in non-volatile memory 40 may be written to non-volatile memory 48, and subsequently decremented in non-volatile memory 48 by control module 46 as equipment 41 is used. When a utilization limit reaches zero, control module 46 sends a disabling message to power supply module 49, thereby preventing further use of equipment 41. As theretofore described with respect to FIG. 3, control module 46 may be programmed to issue a change equipment advisory before a utilization limit is reached.

If the medical equipment that is to be used with power supply and control apparatus 42 is known in advance, non-volatile memory 40 may be programmed only with a serial number, thereby greatly reducing the memory requirements of non-volatile memory 40, as well as its size and cost. The serial number may be used by control module 46 to ensure equipment compatibility, as hereinbefore described. Regulation of power supply module 49 may be accomplished by programming parametric data in non-volatile memory 48 for all equipment that will use power supply and control module 42, indexed by the serial number stored in non-volatile memory 40. Such programming should be performed by the manufacturer prior to distribution or during a maintenance service. Thus, control module 46 may read the serial number from non-volatile memory 40, and read the associated parametric data from non-volatile memory 48, and use the parametric data to regulate power supply module 49 as hereinbefore described. Fault detection may be accomplished in a similar manner.

Similarly, utilization limits for all equipment that will use power supply and control apparatus 42 may be programmed in non-volatile memory 48, indexed by the serial number stored in non-volatile memory 40. As hereinbefore described, control module 46 may track the utilization of all equipment using power supply and control apparatus 42, either by separately storing the accumulated utilization history for each equipment component in non-volatile memory 48, or by decrementing the utilization limits. Control module 46 will disable power supply module 49 when utilization limits have been exceeded, using the principles heretofore described.

EXAMPLE 1

Figure 5:
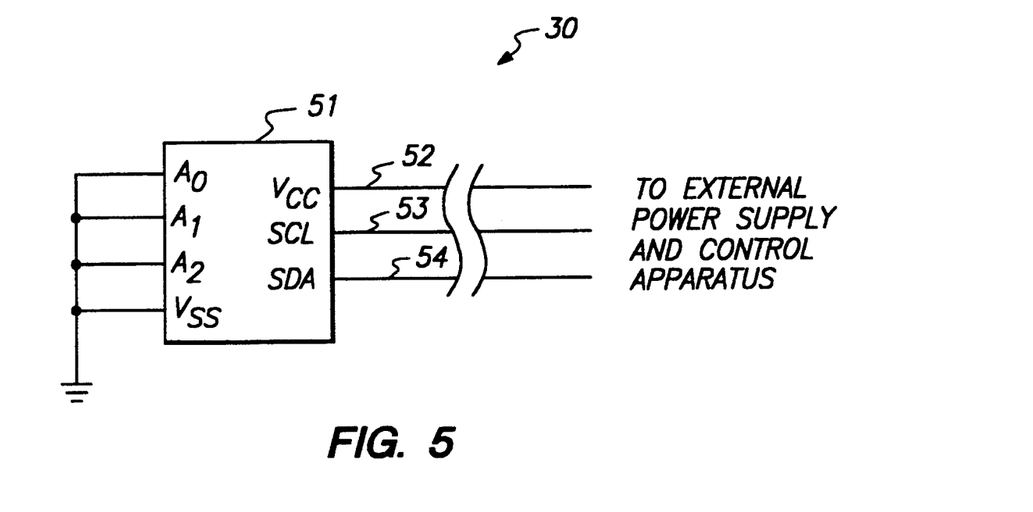
FIG. 5 is a schematic of a non-volatile memory device in accordance with the present invention.

Referring to FIG. 5, an illustrative non-volatile memory device suitable for use as non-volatile memory 30 in the embodiment heretofore described with respect to FIG. 3, or as non-volatile memory 48 in the embodiment heretofore described with respect to FIG. 4, is shown. Non-volatile memory 30 comprises commercially available electrically erasable programmable read only memory (EEPROM) 51. An illustrative EEPROM suitable for use in accordance with the principles of the present invention is the NM24C02 2048-bit serial EEPROM available from National Semiconductor Corporation of Santa Clara, Calif. Table 1 provides a non-exhaustive list of several other EEPROMs that may be used in the present invention. In order to meet the objectives of the present invention, the EEPROM preferably includes at least 1 Kb of memory.

TABLE 1

| Manufacturer | Location | Part No. |
| --- | --- | --- |
| Microchip Technology, Inc. | Chandler, AZ | 24C02 |
| Xicor, Inc. | Milpitas, CA | X24C02 |
| Western Microtechnology | Saratoga, CA | WD24C02 |
| Catalyst Semiconductor, Inc. | Santa Clara, CA | CAT24C02 |

An illustrative three-wire circuit configuration for EEPROM 51 is shown in FIG. 5. Supply input voltage $V_{CC}$, serial clock input SCL and serial data input/output SDA are separately connected to an external control module by connecting wires 52, 53 and 54, respectively. Serial clock input SCL clocks all data into and out of EEPROM 51, while serial data input/output SDA transfers all data into and out of EEPROM 51. Connecting wires 52, 53 and 54 may be disposed within connecting cable 13 or within electrical connectors 14 and 22, described heretofore with respect to FIGS. 1 and 2, that are used to connect the equipment to the external power supply and control apparatus. Supply input $V_{CC}$ is supplied with a constant +5 volts to power EEPROM 51 during operation.

Address pins $A_0$, $A_1$ and $A_2$ are connected to ground, so that the equipment containing EEPROM 51 is addressed as "000" by the external control module. Grounding pin $V_{SS}$ is also grounded. It is contemplated that all medical equipment utilizing the non-volatile memory of the present invention will have a common grounding lead disposed within the connecting cable and electrical connectors used to connect the equipment to the external power supply and control apparatus.

EEPROM 51 supports serial data transfers initiated by an external control module. The SCL input clocks all data transfers into and out of EEPROM 51, in accordance with a clock signal sent via connecting wire 53 from the control module. All data transfers into and out of EEPROM 51 are sent through bi-directional serial data input/output pin SDA.

EEPROM 51 is a "slave device", in the sense that all data transfers into and out of EEPROM 51 via serial data input/output pin SDA are controlled by a "master device", in this case, the external control module. EEPROM 51 responds to a transmission request after receiving a start condition bit and an address bit sequence that corresponds to the address input levels A0, A1 and A2. The address bit sequence is followed by a read/write bit, which determines whether EEPROM 51 is to receive or transmit data. A word address bit sequence typically follows the read/write bit, then data is transferred to or from EEPROM 51.

EXAMPLE 2

Figure 6:
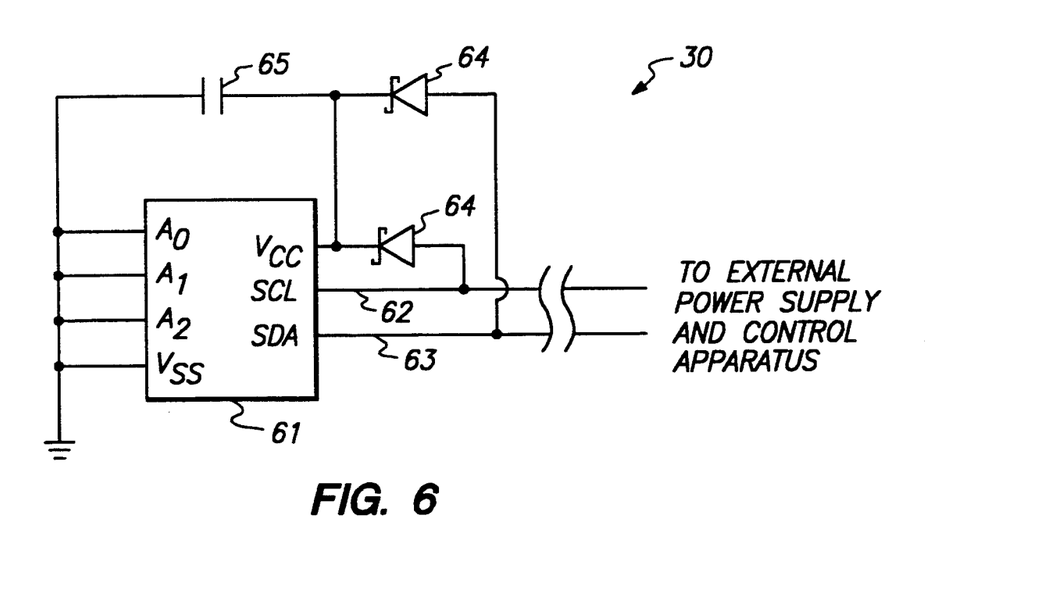
FIG. 6 is a schematic of an alternative embodiment of the in-device memory described with respect to FIG. 5.

FIG. 6 depicts an alternative circuit configuration for non-volatile memory 30 employing the EEPROM described in Example 1 and only two connecting wires. This configuration advantageously permits reduction in the thickness of the cable since fewer connecting wires are required. Furthermore, reducing the number of connecting wires decreases the likelihood of device failure, since there are fewer wires subject to deterioration.

Supply input $V_{CC}$ of EEPROM 61 in FIG. 6 is connected to serial clock input connecting wire 62 and serial data input/output connecting wire 63 by a pair of low forward voltage drop diodes 64, also known as Schottky diodes. Capacitor 65, connected between supply input $V_{CC}$ and ground, is charged by intermittent high voltages supplied by the external control module on serial clock input connecting wire 62 and serial data input/output wire 63. Thus, capacitor 65 is used to maintain a substantially constant supply voltage of +5 volts to supply input $V_{CC}$, without the need for separate supply wire 52 employed in the embodiment described heretofore with respect to FIG. 5.

EXAMPLE 3

Figure 7:
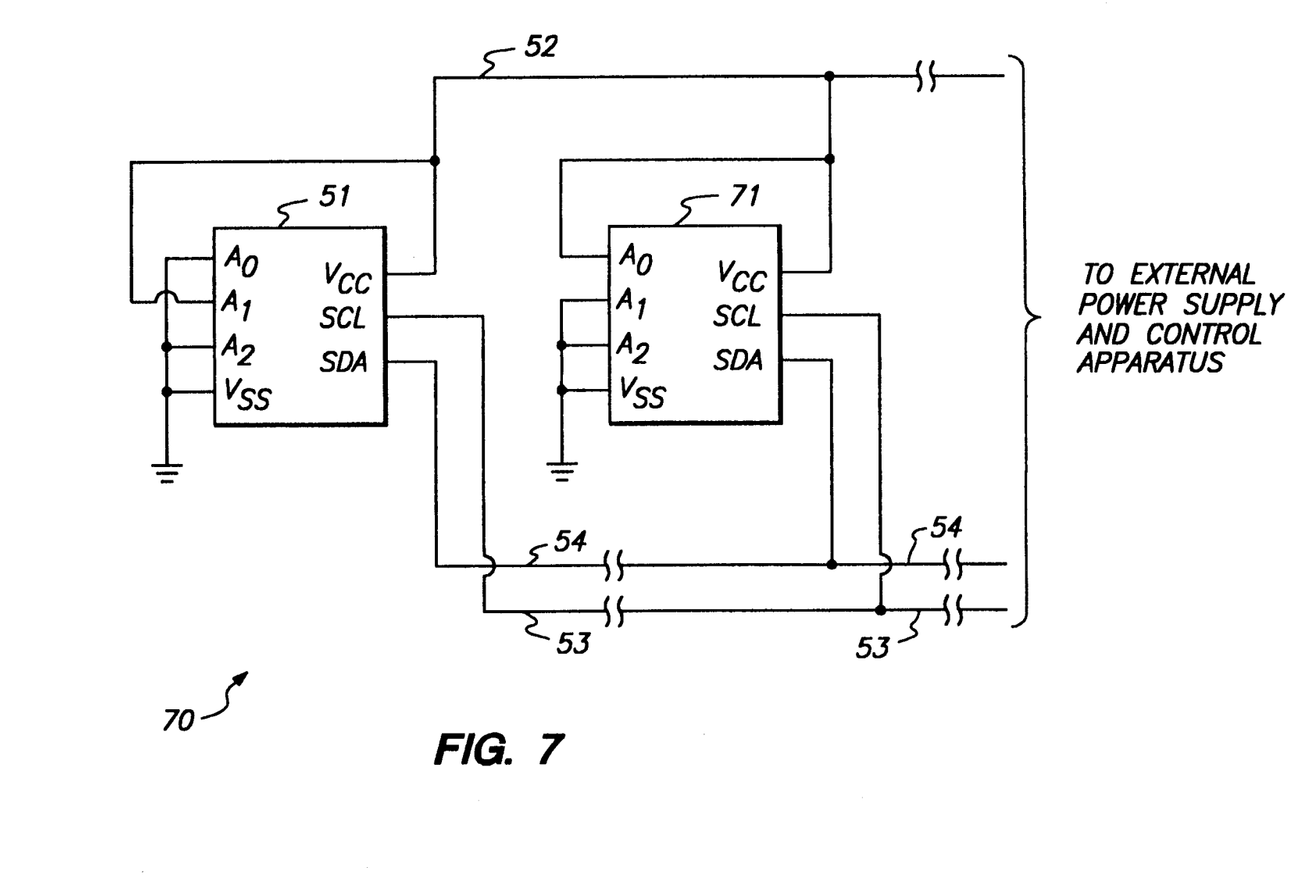
FIG. 7 is a circuit diagram showing two components of an electrically powered medical instrument connected to the same communication bus.

Referring to FIG. 7, an illustrative circuit configuration 70 is described wherein two independently addressable components of a multi-component medical instrument share a common communication bus using the three-wire configuration shown in FIG. 5. EEPROM 51 may be disposed within a handle of the medical instrument, and EEPROM 71 may be disposed within electrical connector 22 of connecting cable 20 shown in FIG. 2. Address pins $A_0$ and $A_2$ of EEPROM 51 are grounded, and address pin $A_1$ is connected to the supply voltage. Thus, EEPROM 51 is addressed as "010". In contrast, address pin $A_0$ of EEPROM 71 is connected to the supply voltage, and address pins $A_1$ and $A_2$ of EEPROM 71 are grounded. Thus, EEPROM 71 is addressed as "001". Using three address bits in this manner, eight independently addressable devices may be configured to share a common communication bus, and the external control module may read from and write to each component independently.

EXAMPLE 4

An illustrative non-volatile memory device suitable for use as non-volatile memory 40 heretofore described with respect to FIG. 4 is the DS2400 Silicon Serial Number manufactured by Dallas Semiconductor Corporation of Dallas, Tex. The DS2400 is preprogrammed by the manufacturer with a 48-bit serial number and an 8-bit model number. A one-wire protocol comprising four states is used to communicate with the DS2400. In the first state, an external control module sends a reset pulse to the DS2400. In the second state, the external control module sends a command word to the DS2400, which must be recognized by the device in order for it to subsequently transmit data. In the third state, the DS2400 transmits the 8-bit model number. In the fourth state, the DS2400 transmits the 48-bit serial number. The DS2400 also sends an 8-bit cyclic redundancy check value which may be used by the external control module to ensure an error-free read.

The serial number stored in the DS2400 may be used by the external control module to ensure equipment compatibility. In order to accomplish the objectives of power supply regulation, fault detection and equipment usage regulation, parametric data and utilization limits must be stored in second non-volatile memory located elsewhere in the equipment, preferably, in the external power supply and control apparatus, as heretofore described with respect to FIG. 4.

One skilled in the art will appreciate that the present invention can be practiced by other than the described embodiments, and the present invention is limited only by the claims that follow.

What is claimed is:

1. In a medical device selected from a plurality of different types of medical devices, the medical device to be connected to a power supply that supplies an output to the medical device during use, the output of the power supply having selectable voltage and current parameters specific to each one of the plurality of different types of medical devices, the improvement comprising memory means disposed in the medical device for storing identification data identifying the type of medical device connected to the power supply, the selection of the voltage and current parameters of the output determined responsive to the identification data.

2. A medical device as defined in claim 1 wherein the memory means comprises a device having a non-volatile memory.

3. A medical device as defined in claim 1 wherein the identification data comprises data from the group consisting of: serial number, model number and power supply parametric data.

4. A medical device as defined in claim 3 wherein the power supply parametric data comprises data from the group consisting of: voltage limits, current limits, instrument impedance, voltage setpoints, current setpoints, voltage ranges, current ranges and scale factors.

5. A medical device as defined in claim 3 wherein the identification data comprises limit data.

6. A medical device as defined in claim 5 wherein the limit data pertains to use of the medical device in individual procedures, the limit data comprising data from the group consisting of: maximum procedure count, maximum actuation count, maximum accumulated actuation time, maximum sterilization count and maximum fault count.

7. A medical device as defined in claim 1 wherein the information pertaining to the medical device stored in the memory means further comprises utilization data reflecting the most recent use of the medical device.

8. A medical device as defined in claim 7 wherein the utilization data pertains to use of the medical device in individual procedures, the utilization data comprising data from the group consisting of: accumulated procedure count after the most recent procedure, accumulated actuation count after the most recent actuation, accumulated actuation time after the most recent actuation, accumulated sterilization count after the most recent sterilization and accumulated fault count for the medical device during a current surgical procedure.

9. A medical device as defined in claim 1 wherein the memory means is disposed in a reusable portion of the medical device.

10. A medical device as defined in claim 2 wherein the memory means comprises a device selected from the group consisting of: ROM, PROM, EPROM, flash memory, non-volatile RAM, battery-backed-up RAM, EEPROM, magnetic data storage apparatus and optical data storage apparatus.

11. A system of tracking the utilization of a medical device selected from a plurality of different types of medical devices, the medical device connected to a power supply that supplies an output to the medical device during use, the output of the power supply having selectable voltage and current parameters specific to each one of the plurality of different types of medical devices, the system comprising:
  memory means disposed in the medical device for storing identification data identifying the type of medical device;
  control means for receiving the information stored in the memory means, the control means setting the voltage and current parameters of the output responsive to the identification data stored in the memory means; and
  connecting means for coupling the memory means to the control means when the medical device is connected to the power supply.

12. The system as defined in claim 11 wherein the memory means comprises a device having a non-volatile memory.

13. The system as defined in claim 11 wherein the identification data comprises data from the group consisting of: serial number, model number and power supply parametric data.

14. The system as defined in claim 13 wherein the power supply parametric data comprises data from the group consisting of: voltage limits, current limits, instrument impedance, voltage setpoints, current setpoints, voltage ranges, current ranges and scale factors.

15. The system as defined in claim 13 wherein the identification data comprises limit data.

16. The system as defined in claim 15 wherein the limit data pertains to use of the medical device in individual procedures, the limit data comprising data from the group consisting of: maximum procedure count, maximum actuation count, maximum accumulated actuation time, maximum sterilization count and maximum fault count.

17. The system as defined in claim 11 wherein the control means tracks utilization data reflecting the most recent use of the medical device, and second non-volatile memory means for storing the utilization data.

18. The system as defined in claim 17 wherein the utilization data pertains to use of the medical device in individual procedures, the utilization data comprising data from the group consisting of: accumulated procedure count after the most recent procedure, accumulated actuation count after the most recent actuation, accumulated actuation time after the most recent actuation, accumulated sterilization count after the most recent sterilization and accumulated fault count for the medical device during a current procedure.

19. The system as defined in claim 15 wherein the control means tracks utilization data reflecting the most recent utilization of the medical device, the utilization data comprising data corresponding to the limit data for the most recent use of the medical device, and second non-volatile memory means for storing the utilization data.

20. The system as defined in claim 19 wherein the utilization data pertains to use of the medical device in individual procedures, the utilization data comprising data from the group consisting of: accumulated procedure count after the most recent procedure, accumulated actuation count after the most recent actuation, accumulated actuation time after the most recent actuation, accumulated sterilization count after the most recent sterilization and accumulated fault count for the medical device during a current procedure.

21. The system as defined in claim 19 wherein the control means compares the limit data to the corresponding utilization data to determine whether the medical device will exceed a limit value.

22. The system as defined in claim 12 wherein the memory means comprises a device selected from the group consisting of: ROM, PROM, EPROM, flash memory, non-volatile RAM, battery-backed-up RAM, EEPROM, magnetic data storage apparatus and optical data storage apparatus.

23. The system as defined in claim 11 wherein the the memory means further stores utilization data reflecting the most recent use of the medical device, and the control means tracks and updates the utilization data stored in the memory means.

24. The system as defined in claim 23 wherein the identification data comprises data from the group consisting of: serial number, model number and power supply parametric data.

25. The system as defined in claim 23 wherein the identification data comprises limit data.

26. The system as defined in claim 24 wherein the power supply parametric data comprises data from the group consisting of: voltage limits, current limits, instrument impedance, voltage setpoints, current setpoints, voltage ranges, current ranges and scale factors.

27. The system as defined in claim 25 wherein the limit data pertains to use of the medical device in individual procedures, the limit data comprising data from the group consisting of: maximum procedure count, maximum actuation time, maximum accumulated actuation count, maximum sterilization count and maximum fault count.

28. The system as defined in claim 23 wherein the utilization data pertains to use of the medical device in individual procedures, the limit data comprising data from the group consisting of: accumulated procedure count after the most recent procedure, accumulated actuation count after the most recent actuation, accumulated actuation time after the most recent actuation, accumulated sterilization count after the most recent sterilization and accumulated fault count for the medical device during a current procedure.

29. The system as defined in claim 25 wherein the control means compares the limit data to the corresponding utilization data to determine whether the medical device will exceed a limit value.

30. The system as defined in claim 27 wherein the memory means comprises a device selected from the group consisting of: non-volatile RAM, battery-backed-up RAM, EEPROM, magnetic data storage apparatus and optical data storage apparatus.

31. The system as defined in claim 29 wherein the control means disables the medical device when the utilization data equals the corresponding limit data.

32. The system as defined in claim 11 wherein the memory means stores preprogrammed utilization limit data for each of a plurality of parameters and the control means measures each of a plurality of parameters corresponding to the preprogrammed utilization limit data during a current use of the medical device, and decrements the preprogrammed utilization limit data stored in the memory means to reflect usage of the medical device during the current use.

33. The system as defined in claim 32 wherein the control means disables the medical device when the at least one of the preprogrammed utilization limits has been decremented to zero.

34. The system as defined in claim 32 wherein the preprogrammed utilization limit data pertains to use of the medical device in individual procedures, the programmed utilization limit data comprising data from the group consisting of: maximum procedure count, maximum actuation count, maximum accumulated actuation time, maximum sterilization count and maximum fault count.

35. The system as defined in claim 13 wherein the identification data comprises power supply parametric data and the control means reads the power supply parametric data stored in the memory means; and regulates the power supplied to the medical device in accordance with the power supply parametric data.

36. The system as defined in claim 35 wherein the parametric data comprises data from the group consisting of: maximum current, maximum voltage, instrument impedance, power supply scale factors for limiting the power supplied to the medical device to an acceptable range, voltage setpoints and current setpoints.

37. The system as defined in claim 11, wherein the control means stores a preprogrammed list of identification codes for each one of the plurality of different types of medical devices compatible with the power supply, receives the identification data from the memory means, compares the identification data received from the memory means to the preprogrammed list of identification codes and disables the medical device if the identification data does not correspond to any identification code.

38. The system as defined in claim 13, wherein the identification data further comprises a maximum fault limit for faults occurring during use and the control means counts the number of faults occurring during a current use, receives the identification data from the memory means, compares the identification data received from the memory means to the number of faults counted during the current use and prevents the medical device from being reset if the number of faults counted during the current use exceeds the maximum fault limit.

39. The system as defined in claim 11 wherein the control means comprises a microprocessor.

40. The system as defined in claim 11 wherein the control means further comprises random access memory means.

41. The system as defined in claim 11 wherein the control means is disposed within the power supply.

42. The system as defined in claim 17 wherein the second non-volatile memory means comprises a device selected from the group consisting of: non-volatile RAM, battery-backed-up RAM, EEPROM, magnetic data storage apparatus and optical data storage apparatus.

43. The system as defined in claim 21 wherein the control means disables the medical device when the utilization data equals the corresponding limit data.

44. The system as defined in claim 19 wherein the second non-volatile memory means comprises a device selected from the group consisting of: non-volatile RAM, battery-backed-up RAM, EEPROM, magnetic data storage apparatus and optical data storage apparatus.

45. The system as defined in claim 21 wherein the control means issues a change equipment advisory before the medical device has exceeded a limit value.

46. The system as defined in claim 29 wherein the control means issues a change equipment advisory before the medical device has exceeded a limit value.

* * * * *

UNITED STATES PATENT AND TRADEMARK OFFICE
CERTIFICATE OF CORRECTION

PATENT NO. : 5,400,267  
DATED : March 21, 1995  
INVENTOR(S) : Dennis J. Denen, et al.

Page 1 of 2

It is certified that error appears in the above-indentified patent and that said Letters Patent is hereby corrected as shown below:

| Column | Line | |
|---|---|---|
| 1 | 61 | change "additions" to --addition,-- |
| 1 | 68 | after "for", insert --which the-- |
| 3 | 5 | between "power" and "supply", delete one space |
|   |   | between "measuring" and "apparatus", delete one space |
| 7 | 1 | after "in", insert --conjunction with the accompanying drawings, in which-- |

UNITED STATES PATENT AND TRADEMARK OFFICE
CERTIFICATE OF CORRECTION

PATENT NO. : 5,400,267
DATED : March 21, 1995
INVENTOR(S) : Dennis J. Denen, et al.

It is certified that error appears in the above-indentified patent and that said Letters Patent is hereby corrected as shown below:

| Column | Line | |
|--------|------|---|
| 7 | 2 | delete "conjunction" |
| 7 | 3 | delete "with the accompanying drawings, in which" |
| 19 | 31 | before "RAM", delete --.-- |

Signed and Sealed this

Twentieth Day of August, 1996

Attest:

BRUCE LEHMAN

Attesting Officer     Commissioner of Patents and Trademarks